US008438044B2

(12) United States Patent
Kerrigan et al.

(10) Patent No.: US 8,438,044 B2
(45) Date of Patent: May 7, 2013

(54) SYSTEMS AND METHODS COMBINING PRINT AND AUDIO TECHNOLOGIES TO DELIVER AND PERSONALIZE HEALTH INFORMATION

(75) Inventors: Elizabeth Duffy Kerrigan, Polk City, IA (US); Linda Carol Smith Austin, Charleston, SC (US)

(73) Assignee: Audiahealth, LLC, Charleston, SC (US)

( * ) Notice: Subject to any disclaimer, the term of this patent is extended or adjusted under 35 U.S.C. 154(b) by 0 days.

(21) Appl. No.: 13/343,101

(22) Filed: Jan. 4, 2012

(65) Prior Publication Data

US 2012/0185269 A1    Jul. 19, 2012

Related U.S. Application Data

(60) Provisional application No. 61/433,717, filed on Jan. 18, 2011.

(51) Int. Cl.
*G06Q 50/00* (2012.01)
(52) U.S. Cl.
USPC .......................................... 705/3; 40/124.09
(58) Field of Classification Search .................. 705/2–4; 40/124.09–124.191
See application file for complete search history.

(56) References Cited

U.S. PATENT DOCUMENTS

| | | | |
|---|---|---|---|
| 4,984,158 A | | 1/1991 | Hillsman |
| 5,387,108 A * | | 2/1995 | Crowell .......................... 434/319 |
| 5,577,918 A | | 11/1996 | Crowell |
| 5,852,590 A * | | 12/1998 | de la Huerga ................... 368/10 |
| 6,259,654 B1 * | | 7/2001 | de la Huerga ................... 368/10 |
| 7,395,214 B2 * | | 7/2008 | Shillingburg ....................... 705/2 |
| 7,555,436 B2 | | 6/2009 | Brown |
| 7,715,277 B2 * | | 5/2010 | de la Huerga ................... 368/10 |
| 2005/0168337 A1 | | 8/2005 | Mahoney |
| 2005/0288964 A1 * | | 12/2005 | Lutzen et al. ....................... 705/2 |
| 2007/0210147 A1 * | | 9/2007 | Morrone et al. ............... 235/375 |
| 2009/0217559 A1 | | 9/2009 | Sayre |
| 2009/0259474 A1 | | 10/2009 | Lien et al. |

(Continued)

FOREIGN PATENT DOCUMENTS

| | | |
|---|---|---|
| EP | 1880688 A1 | 1/2008 |
| WO | WO 2007126851 A2 | 11/2007 |
| WO | WO 2008091838 A2 | 7/2008 |
| WO | WO 2010023591 A2 | 3/2010 |

OTHER PUBLICATIONS

Finley, S. (2007). Holt virtual investigations. MultiMedia & Internet@Schools, 14(5), 43-44. Retrieved from http://search.proquest.com/docview/229761414?accountid=14753. Best Proquest NPL result.*

*Primary Examiner* — Mark Holcomb
(74) *Attorney, Agent, or Firm* — McKee, Voorhees & Sease, P.L.C.

(57) ABSTRACT

Systems and methods for delivering health information by combining print and audio information are provided. The systems utilize prerecorded audio systems, with or without recordable audio systems, in conjunction with print material to deliver individualized, patient-specific health information and/or instructions to a patient or caregiver. The method allows patients to collect and retain personalized, voice-recorded health material in the same location as printed and prerecorded health information. The present invention overcomes the limitations of the prior art by to provide to a patient or caregiver the ability to store, record, and deliver audio voice-recorded material along with print material in order to deliver individualized health information.

20 Claims, 4 Drawing Sheets

U.S. PATENT DOCUMENTS

| | | |
|---|---|---|
| 2010/0011632 A1 | 1/2010 | Shields et al. |
| 2010/0063846 A1 | 3/2010 | Shakamuri |
| 2010/0096443 A1* | 4/2010 | Maloney ................. 235/375 |
| 2010/0307036 A1 | 12/2010 | Lien et al. |
| 2010/0308981 A1 | 12/2010 | Lien et al. |
| 2011/0046961 A2 | 2/2011 | Lien et al. |
| 2011/0123971 A1* | 5/2011 | Berkowitz et al. ............ 434/308 |
| 2012/0116794 A1* | 5/2012 | Wilkerson-Amendell ....... 705/2 |

* cited by examiner

SYSTEMS AND METHODS COMBINING PRINT AND AUDIO TECHNOLOGIES TO DELIVER AND PERSONALIZE HEALTH INFORMATION

CROSS-REFERENCE TO RELATED APPLICATIONS

This application is a nonprovisional application of U.S. Provisional Application No. 61/433,717, filed Jan. 18, 2011, which is herein incorporated by reference in its entirety.

FIELD OF THE INVENTION

The present invention relates to systems and methods for storing, recording and delivering prerecorded and recordable information to a patient in need of various types of personalized health information. In a particular embodiment, the invention provides systems and methods to educate and inform patients and caregivers about diseases and other clinically relevant information to a particular patient and/or caregiver.

BACKGROUND OF THE INVENTION

Improving patient adherence to medications and the treatment plan has been identified by many groups, including the World Health Organization, as one of the most important public health goals facing both developed and third world countries. Overall adherence rates are estimated at between 50-80% in the U.S., and poor communication between patients and healthcare providers is an important cause of patients failing to adhere to treatment recommendations. As treatment regimens have become more complex and clinician time has become more limited, an innovative strategy to allow rapidly recordable clinical instructions that support patients' ability to understand, accept, and adhere to treatment regimens has great value.

Currently, materials produced for patient education rely primarily on written material with illustrations. These commonly used materials have a number of drawbacks. While useful for many patients, print materials may not be comprehensible for patients of low literacy or limited health knowledge. These materials may not be individually customized according to a patient's needs and generally do not incorporate information from multiple healthcare professionals. They cannot include complex information communicated orally to the patient by the healthcare provider.

Combining print and recordable or pre-recorded information using audio technology embedded in a print medium could offer a powerful means to educate patients. From the patient's perspective, information recorded in their provider's voice can convey personal concern, encouragement, and a sense of urgency while also explaining complex information. This information can be both read and re-listened to at home by the patient and family as many times as necessary. From the clinician's perspective, a far more detailed and personalized set of instructions can be transmitted much more quickly than if it were written or typed, since one minute of voice information is equal to roughly one page of double-spaced information. Further, the recordable function could allow family members to record information or questions that can be communicated to the clinician at a subsequent visit. The device could also be used to record a patient's own commitment to a particular health goal as part of an ongoing health-coaching relationship.

Such a system could have great utility in a variety of heath settings. In outpatient clinics, the card could be brought to every visit to have new instructions re-recorded on it and to transmit questions from the family to the clinician. In a hospital setting, the card could be left at the bedside so that a physician can leave a daily update for the family during bedside rounds, or hear questions that the family has recorded for the physician. At the time of hospital discharge, so-called "medication reconciliation" could be recorded on the card so that patients and families would have clear discharge instructions. In a health coaching setting, both the coach and the patient could record goals and commitments on the card.

Accordingly, it is an objective of the claimed invention to provide methods and a system that combines audio technology with print material to deliver health information personalized to the individual patient that permits the interaction of written and verbal information.

It is a further objective of the claimed invention to provide methods and a system that allows for audio voice-recording by multiple individuals, including doctors, nurses, pharmacists, other healthcare providers, and patients to achieve the desired clinical outcomes applicable to the particular patient.

It is a further objective of the claimed invention to provide methods and a system that allows prerecorded or previously recorded audio voice-recordings to be added to so that more general material can be specifically tailored to individual patients.

It is a further objective of the claimed invention to provide methods and a system that permits separate and independent use of the written and audio technology and materials.

It is a further objective of the claimed invention to provide methods and a system that allows recorded patient healthcare goal commitments to their treatment and or care plan.

It is still further an objective of the claimed invention to provide to a patient in need the ability to store, record, and deliver audio voice-recorded material along with print material in order to deliver individualized health information.

BRIEF SUMMARY OF THE INVENTION

The invention overcomes the problems with the prior art technology, as well as other problems as will become apparent herein. One aspect of the current invention comprises, consists of and/or consists essentially of a system that combines written materials with audio technology that allows for the contemporaneous delivery of both written and audio health information to improve health-related outcomes of a patient.

According to a particular embodiment of the invention, the system for combining audio technology with print material to deliver health information comprises: a microprocessor; a power source; a speaker; and a housing for said system further comprising print material. The system may also comprise, consist of and/or consist essentially of a microphone.

According to an additional embodiment the microprocessor may comprise a complementary metal oxide semiconductor. Still further, the system may house a single microprocessor with prerecorded voiced information about health information or instructions or may house multiple microprocessors each (with or without prerecorded content). According to an embodiment of the systems, the microprocessors may be affixed to a cardboard, paper card or the like housing an adhesive. In addition, or in the alternative, the microprocessors may be contained in slots within a card housing.

According to an embodiment, the print material of the system may include a booklet, pamphlet, cardboard or paper sheet, photograph(s), drawings, other graphic material or the like containing printed information for the patient and/or allow marketing or branding of a provider. According to an embodiment, the print material includes space for a patient to chart or make notes.

According to an additional embodiment of the present invention, novel methods are presented allowing individuals the ability to collect and record audio information from multiple sources in a single location that also provides written material. According to a preferred embodiment of the invention, these methods comprise, consist of and/or consist essentially of providing a prerecorded audio source along with a recordable audio source together in a housing that also includes print materials to a patient.

According to a particular embodiment of the invention, the methods for storing, recording and delivering audio technology with print material to deliver health information to a patient in need thereof, comprises: providing a prerecorded audio source; and providing means for a recordable audio source; wherein said prerecorded and recordable audio sources are housed in an system for providing print material and provided to a patient in need thereof. The methods may further include providing audio technology and print materials to a patient or caregiver in need of education or counseling about a disease, condition or other clinically relevant information. Still further, the methods may include use of a pre-recorded audio source and/or recordable audio source, wherein the prerecorded audio source is selected from the group consisting of microprocessors, embedded systems, and technology using integrated circuits. The methods may also include use of print material, wherein the print material is selected from the group consisting of paper sheet, booklet, pamphlet, cardstock and combinations thereof.

According to the invention, both the systems and methods comprise, consist of and/or consist essentially of combinations of printed educational materials and audio technology to be used together to convey and collect information about health, wellness and/or the provider to improve the health outcomes of the patient.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
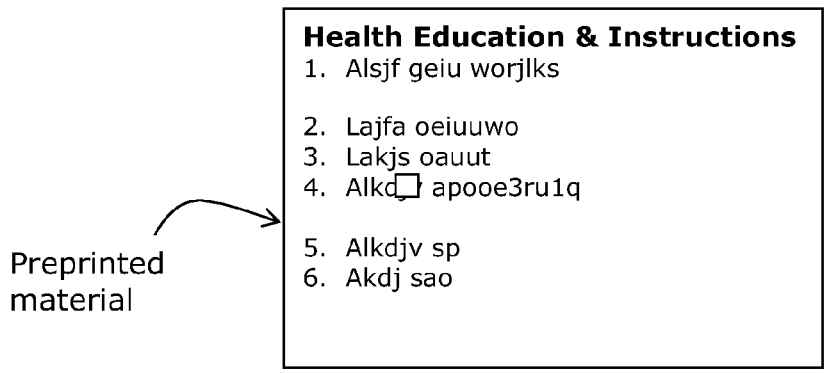
FIG. 1 is a non-limiting perspective anterior view of one embodiment of a housing for the systems according to the invention, wherein the system comprises written material, and wherein the written material is preprinted material prepared with information about a health provider, a specific health condition or conditions, a medical procedure or procedures, and/or medical instructions.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The invention described herein supplements pre-printed material with audio voice-recorded material to allow patients, family members, and caregivers—including those of low literacy—to better understand and care for a patient's particular health condition. Accordingly, the invention provides systems and methods for storing, recording, and delivering both prerecorded and recordable information to a person in need thereof. The recordable feature allows healthcare providers to quickly relay individual instructions or explanations. According to various embodiments of the invention, the recordable feature also allows for the patient to record in their own words, their treatment instructions, medication requirements, commitments to their care protocol or care plan.

As used herein, healthcare provider includes for example a doctor, pharmacist, nurse, pharmaceutical company, or other company providing health-related content to patients and/or caregivers.

The use of audio, written, and picture information allows a wide range of patients and/or caregivers choice of the learning modality most suited to their learning preference.

In some aspects, the systems and methods of the invention include one or more written, one or more prerecorded, and one or more recordable components. In addition, some patients at the time of care may not be ready to accept information. For example, it could be the first time a patient is told of their disease condition and their mental state is not ready to understand what the healthcare provider is communicating. Voice-recorded information will allow the patient to listen to the instruction or explanation at a later time when they are more mentally able to accept information and thereafter on a repetitive basis to remind and/or re-emphasize the instruction or explanation.

Systems for Combining Audio Technology with Print Material

According to an embodiment of the invention, the system comprises a housing 1 for an audio device that comprises at least one source for printed material 2, and at least one source for one or more audio devices 3. (As shown in a non-limiting embodiment of the invention in FIG. 5).

In an exemplary embodiment, the housing is a card constructed of two pieces of cardstock, affixed to form a single sheet with a void in the middle, having a front and back panel upon which material can be printed. In another embodiment, the housing is folded one or more times to provide multiple panels upon which material can be printed. In yet another embodiment, the housing is in the form of a presentation or document-retaining folder of generally conventional construction, having one or more pockets into which additional printed material in the form of papers, advertising, written instructions, business cards, and the like can be inserted. In yet another embodiment, the housing is constructed of plastic, forming a case onto which material can be printed, or into which printed material can be inserted. Exemplary housing suitable for use according to the present invention is described, for example, in U.S. Pat. Nos. 5,577,918 and 5,387,108, which are incorporated herein by reference in its entirety.

In a further exemplary embodiment, the housing is a mobile application that comprises at least one source for printed material, and at least one source for one or more audio devices. For example, without being limited to a particular theory of the invention, a housing for use of a mobile application of the invention may include a tablet computer (e.g. iPad®) or alternative audio-visual media. Additionally suitable housings may include smartphones, laptop computers, e-readers and the like. Such housings still comprises at least one source for printed material within the device (e.g. pre-printed material or material added by a user/patient), and at least one source for one or more audio devices. According to an embodiment of the invention, a mobile application allows the patient to access both the printed material and audio material in similar manners as other embodiments the invention, with the additional benefits afforded by the particular mobile application.

Print or written components 2 for use in the present invention include, but are not limited to, printed material in the form of paper sheet, booklet, pamphlet, cardstock, electronic media or combinations of the same. In an exemplary embodiment, the print material comprises information about a healthcare provider, specific health condition or conditions, medical procedures, medical instructions, combinations of the same or the like. In another embodiment, the printed material further comprises space for a patient or caregiver to chart content and/or make notes (e.g. daily symptoms) or clinical information. According to an embodiment of the invention the print or written materials includes the capability of a diary, journal, log or the like for a patient. In a more preferred embodiment, the print materials further comprise material that permits the user to access additional information, such as for example, a matrix, two-dimensional barcode and/or internet or other electronic or web-based access according to the particular embodiment of the housing according to the invention.

The audio device 3 preferably includes combinations of a microphone 4, a speaker 5, a microprocessor 6, a power supply 7, and first, second, and third switches 8, 9, and 10. As would be recognized by one skilled in the art, the microphone and switches are implicit to a recordable audio system in order to affect its functionality. Accordingly, these components supplement the disclosure of Provisional Application No. 61/433,717. In addition to the electronic components mentioned, which are coupled to the microprocessor 6, other electronic components may be included in the audio device as would be readily understood and appreciated by one of ordinary skill in the art. For example, one or more light emitting diodes (LED) could be integrated to give the user a visual indication that one of the functions has been activated.

Figure 5:
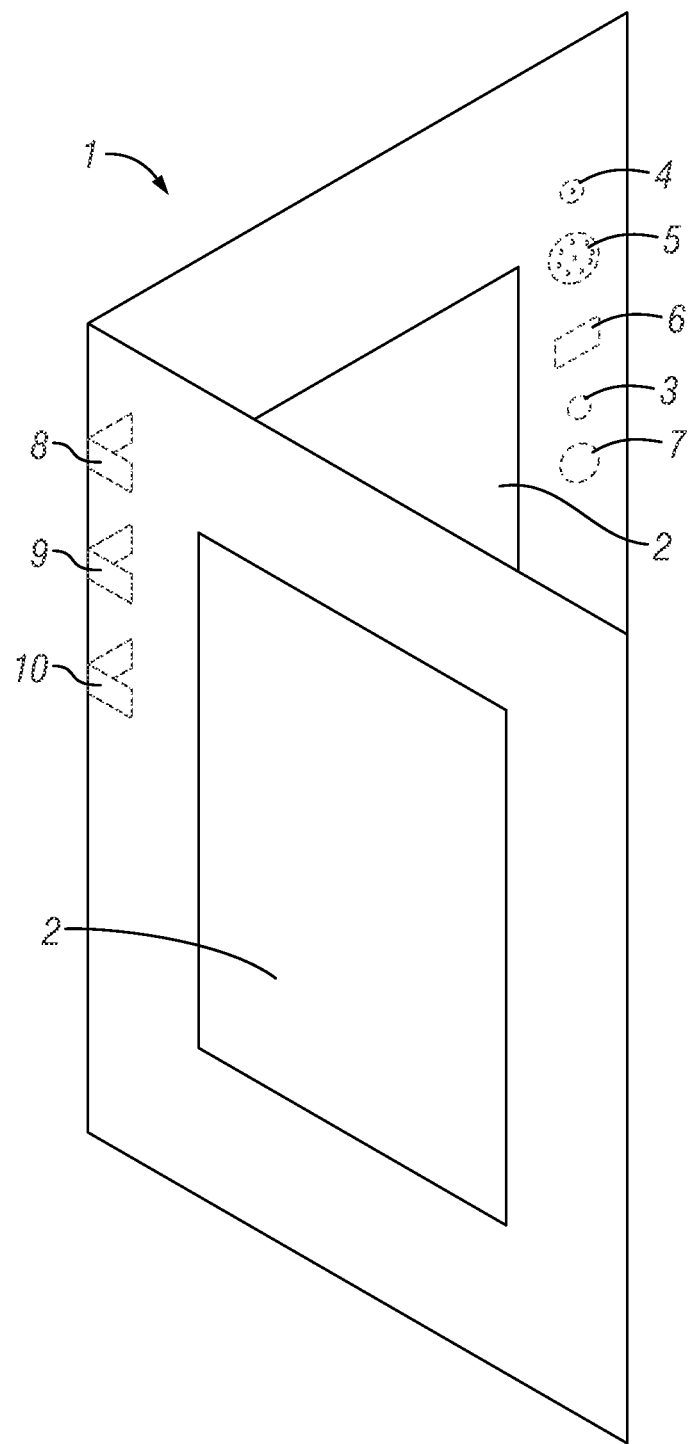
FIG. 5 shows a single non-limiting physical embodiment of the invention wherein a system includes a housing 1 for an audio device, containing print material 2, and an audio device 3. The system may further include a microphone 4, a speaker 5, a microprocessor 6, a power supply 7, and first, second, and third switches 8, 9, and 10.

The depiction of the various elements of the housing shown in FIG. 5 are non-limiting. For example, the various components may be located in any arrangement or formation—not limited to the depiction of the figure. For example, there may be more than one of each of the elements depicted in the figure. In addition, the location of the various components (3, 4, 5, 6, 7, 8, 9 and 10) may vary according to a particular embodiment. For example, it may be desirable to have the various components in the inside of the housing 1 or on the outside of the housing 1.

In an exemplary embodiment, the audio device 3 includes a separate microphone 4 and speaker 5. As would be understood by one skilled in the art, the microphone and speaker could be replaced by a single combination microphone/speaker device. An audio system comprising a microphone suitable for use according to the present invention is described in U.S. Pat. No. 5,387,108, which is herein incorporated by reference in its entirety.

The microprocessor 6 of the present invention includes any audio message recording and playback means as one skilled in the art would appreciate. The microprocessor may comprise an integrated circuit chip. In a preferred embodiment the microprocessor may comprise a complementary metal oxide semiconductor. A microprocessor comprising a circuitry capable of receiving, retaining, and delivering audible messages suitable for use according to the present invention is described in further detail, for example, in U.S. Pat. No. 5,577,918, which is herein incorporated by reference in its entirety.

According to the various embodiments of the invention, the systems of the present invention, namely the audio device 3, are capable of recording and playing back varying lengths of audio content. According to an embodiment of the invention, at least thirty seconds of material may be recorded and played back for a patient or care giver. In a more preferred embodiment, the system can record and play back at least more than one minute of material. In an even more preferred embodiment, the system can record and play back at least more than two minutes of material. Still further, according to a most preferred embodiment, the systems of the invention can both record and play back any length of audio material necessary to provide the needed healthcare instructions or information.

According to a further embodiment of the invention, the systems of the present invention, namely the audio device 3, are further capable of recording and playing back more than one source of recorded information. For example, the audio device may allow the use of various recordings which a patient and/or caregiver may play back upon demand. Such outcomes are achieved through the use of skill and information readily available to one of skill in the art and are not intended to limit the particular scope of the application.

As would be appreciated by one of ordinary skill in the art, prerecorded and recordable components for use in the present invention include, but are not limited to, audio technology, including microprocessors, embedded systems, and any technology using integrated circuits. In an exemplary embodiment, the microprocessor 6 is connected to the microphone, speaker, power supply, and switches to provide the means for receiving, retaining, and retrieval of audio information as is well known by those of ordinary skill in the art.

In a preferred embodiment, the power source 7 of the present invention comprises a plurality of batteries that are interconnected and connected to the microprocessor to provide the desired power thereto. As one skilled in the art will appreciate, the power source used according to the invention may include solar batteries, kinetic energy harvesters, external power adapters, combinations of the same or the like. Other power sources could be employed, as would be appreciated by one of ordinary skill in the art and are embodied in the scope of the present invention.

The microphone 4, speaker 5, microprocessor 6, and power source 7 allow the audio system to contain a plurality of prerecorded audio sources and recordable audio sources. In a preferred embodiment, the system comprises both prerecorded and recordable audio technology.

The first switch 8 is configured to activate the recording feature of the audio device. Accordingly, in the illustrated embodiment (FIG. 3), the first switch is implemented as a record button. As would be appreciated by one of ordinary skill in the art, pressing the record button initiates a recording session whereby a verbal message may be recorded onto the audio device by way of the microphone component. The recording session is terminated by releasing the record button. In the alternative, the recording session can be terminated by pressing the record button a second time. An exemplary audio system comprising a switch suitable for use according to the present invention is described in U.S. Pat. No. 5,387,108, incorporated herein by reference in its entirety.

The second switch 9 is configured to activate and deactivate the playback feature of the audio device. Accordingly, in the illustrated embodiment (FIG. 3) the second switch is implemented as a play/stop button. As would be appreciated by one of ordinary skill in the art, pressing the play/stop button once would activate the play function of the audio device, allowing the individual to listen to the recorded verbal message. Pressing the play/stop button a second time deactivates the play function, and resets the audio device for playback.

According to a preferred embodiment, a third switch 10 may be configured in various embodiments of the invention to activate the add recording function. This function allows the user to add additional voiced-recorded material to that already recorded on the audio device. In an alternative embodiment, the third switch provides an overwrite function that allows the user to record over voice-recorded information already contained on the audio device, thereby replacing the preexisting voice-recorded material with new voice-recorded material. As would be appreciated by one of ordinary skill in the art, additional switches could be included to provide multiple combinations of the play, stop, record, add recording, and/or overwrite functions. Such variations in the embodiments of the invention are included within the scope of the present invention.

The recordable components of the audio device 3 for use in the present invention include, but are not limited to, microprocessors, embedded systems, and any technology using integrated circuitry. According to an embodiment of the invention, all circuitry is flexible. According to an exemplary, non-limiting embodiment of the invention, both prerecorded and recordable components can be prerecorded or recorded using a microprocessor connected to a microphone, power source, and speaker.

According to the invention, the audio device 3, including both the prerecorded and recordable audio sources, are housed in the system which further provides a print material source 2. The housing 1 for such a system according to the invention may surround or enclose the various components of the audio device 3, including, for example, the microphone, microprocessor, power source and/or speaker in a variety of ways in order to support, protect and/or position the audio device components.

According to the invention, there can be one or more audio device components 3 combined with the print material 2. For example, there might be an individual microprocessor with appropriate recorded content for each of several co-occurring illnesses a patient might have. A single piece of print material might contain one or more microprocessors containing prerecorded material, and a second microprocessor that could be used for recording patient-specific information. A further embodiment may include print or branded materials with no prerecorded information but a recordable device for a healthcare provider to communicate or relay patient specific or disease information. In addition, included in the scope of the invention are variations of the combinations set forth herein for combining audio technology with print material as would be appreciated by one of ordinary skill in the art.

In one embodiment, the invention comprises, consists of and/or consists essentially of a housing with printed material peripherally surrounding, supporting, and enclosing an audio device upon which voice-recorded material has been prerecorded. In a preferred configuration, the audio device is affixed within an interior void formed by two pieces of cardstock adhered together to form a single sheet. It is understood that a single sheet could also be formed by folding a single piece of cardstock. It is further understood that multiple voids could be formed by adhering multiple pieces of cardstock together or folding a single piece of cardstock multiple times, or combinations thereof, thereby providing enclosure into which multiple audio devices could be affixed. The material on the audio device can be played back using the play/stop button. A second audio device, also embedded in the housing, contains no prerecorded material and is capable of receiving, retaining, and retrieving voice-recorded material by the use of a second set of buttons, comprising both a record and play/stop button.

In another embodiment, a single audio device is similarly enclosed within the housing upon which voice-recorded material has been prerecorded, and which is also capable of receiving, retaining, and retrieving additional voice-recorded material by use of the add recording and play/stop buttons.

In yet another embodiment, a single audio device is embedded into the housing upon which voice-recorded material has been prerecorded, and which can be recorded over by use of an overwrite function. In this embodiment, the functionality of the audio device is controlled by a play/stop button, a record/overwrite button, and add recording buttons.

In yet another embodiment, the audio device is embedded in the housing, but does not contain any prerecorded material. In this embodiment, the audio device is capable of receiving, retaining, and retrieving voice-recorded material by use of the record, play, and add functions controlled by the corresponding buttons. Alternatively, this embodiment could include the ability to overwrite the voice-recorded material through use of an overwrite function controlled by a separate button.

In yet another embodiment the audio device is contained in a pocket or compartment in the print material housing that permits the audio device to be separated from and have independent functionality from the print materials. It is understood that such a separable audio device could be contained inside separate housing. It is further understood that the audio device could include both prerecorded and recordable microprocessors.

Voice-recorded information as used herein includes a variety of health-related information, including for example, medication instructions, discharge or transition care directions, explanations of signs and symptoms of illness, physical and other therapy suggestions, pharmaceutical information including drugs, dosages, and side effects, appointment reminders, provider information, combinations of the same and the like. Such information may be recorded by a healthcare provider or other caregiver, or the patient or another individual acting for the patient. In an exemplary embodiment, the prerecorded information is provided by a drug company or other healthcare-related company. In another embodiment, the voice recorded information is provided by a physician, nurse, pharmacist, other healthcare professional or combination of the same. In yet another embodiment, the voice-recorded information is provided by the patient or a caregiver.

It should also be noted that, as used in this specification and the appended claims, the systems according to the invention can be configured or arranged in a variety of ways in order to construct a system capable of combining audio technology with print material.

The various embodiments of the invention disclosed herein can be arranged, configured, constructed and/or adapted to meet the specifications of a particular system based upon the enabling disclosure of the invention.

Methods for Storing, Recording and Delivering Audio Technology with Print Material Another aspect of the present invention is a method for storing, recording and/or delivering various forms of audio technology with print material to deliver health information to a patient and/or caregiver in need thereof. This method comprises the steps of providing a prerecorded audio source and means for a recordable audio source to a patient or caregiver; providing print material to said patient or caregiver; wherein said prerecorded and recordable audio sources are housed in an system for providing print material to deliver health information about health, wellness, prescriptions and/or a disease state or condition of said patient, and wherein the system comprises at least one microprocessor, a power source, a speaker, and a housing. This method, including the various embodiments of the methods according to the invention, allows patients to collect and retain personalized, voice-recorded health material in the same location as printed and prerecorded health information, thereby overcoming problems with the prior art technology.

According to an embodiment, generic and/or unique, patient-specific information can be recorded to the audio device through the microprocessor using the battery, microphone, and speaker and as described according to the systems of the invention. The voiced prerecorded or recorded material is activated using the on off switch when in the on position and turned off when in the off position. The means for a recordable audio source, as described above, are known and would be appreciated by one of ordinary skill in the art.

Delivery of health information to educate and inform patients and caregivers is critical to patient healing and management of their disease. This invention combines two means of delivery of information, print and audio. In an exemplary embodiment, method according to the invention could be implemented by providing a device in the form of a folded card or brochure that contains pre-printed material describing a patient's diagnosis with an embedded or attached microprocessor offering a voice-recorded description of these elements. The provided device can be used to deliver further health information by incorporating additional material, in either print or audio form, as provided by the patient and/or the caregiver. The embodiments of the methods according to the invention thereby allow the incorporation of multiple sources of print and audio health material for delivery to a patient and/or caregiver in need thereof.

The print material may comprise a paper sheet, booklet, pamphlet, cardstock, plastic housing, combinations of the same or the like as described herein and appreciated by one of ordinary skill in the art. In another embodiment, a system or device provided according to the invention could be a flat cardboard or paper card, containing preprinted material with a grid for patient's notes, and the embedded recording microprocessor would allow the physician or other healthcare provider to dictate comments that the patient and family could listen to at another time. In another embodiment, the provided device would be a card with an affixed refrigerator magnet, with print, pictures, and recorded material giving instructions for a patient's diet. In yet another embodiment, the provided device would be a plastic case into which both the printed material and audio source can be easily inserted and removed.

EXAMPLES

Embodiments of the preset invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

A method for storing, recording and delivering prerecorded and recordable information to educate a patient or person in need thereof includes first preparing a housing comprising preprinted material with information about a health provider, specific health condition or conditions, medical procedure or medical instructions (FIG. 1). The preprinted material includes both information and an area for additional information to be added. The housing envelopes the audio device in such a manner that the audio device is affixed and embedded within the housing and not visible.

Figure 2:
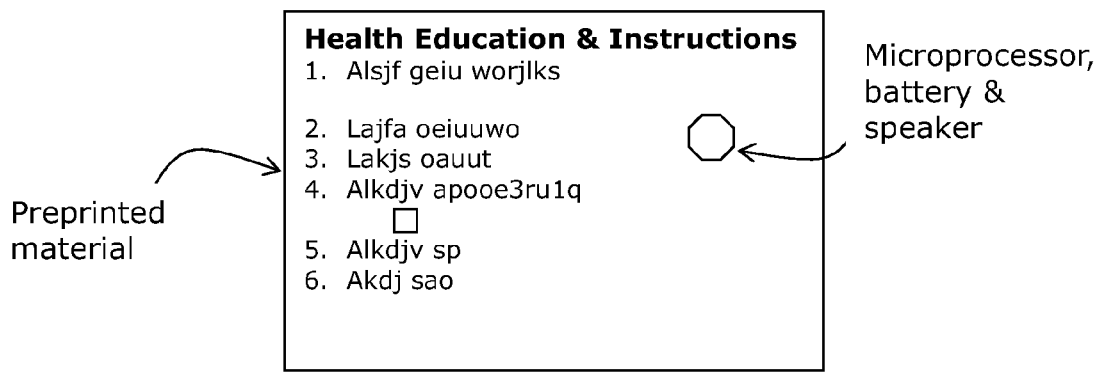
FIG. 2 is a non-limiting perspective anterior view of one embodiment of a housing for the systems according to the invention wherein an audio device comprises a prerecorded microprocessors with attached battery and miniature speaker affixed to the print material (e.g. housing for the system). The embodiment of the invention shows the affixed portions for convenience without limiting the manner in which the microprocessor, battery and speaker may be affixed.

A prerecorded audio device, comprising a microprocessor with attached battery and miniature speaker are then affixed to the print material (FIG. 2). The prerecorded audio device is operated by a switch, implemented as a play/stop button. This permits the patient to play back the voice-recorded material prerecorded on the audio device in the context of the print material provided on the housing.

Figure 3:
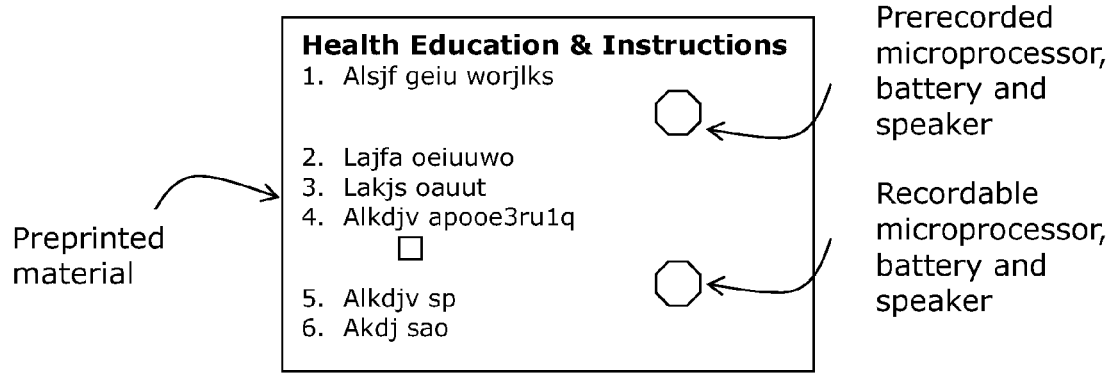
FIG. 3 is a non-limiting perspective anterior view of one embodiment of a housing for the systems according to the invention wherein an audio device is combined with print materials, in particular a system including a plurality of microprocessors, batteries and speakers, shown as including both a recordable and a prerecorded audio device attached to the print material (e.g. housing for the system). The recordable audio device comprises a recordable microprocessor attached, which would further include a power source, a speaker, a microphone, and three switches implemented as buttons with different functionalities for recording content.

In addition, a recordable microprocessor is attached to and embedded in the print material (FIG. 3). The recordable audio device is operated by the three switches, implemented as a play/stop button, a record button, and an add recording button. The record button permits an individual physician, nurse, pharmacist, or other healthcare provider, or an individual patient to add additional individualized, patient-specific voice-recorded material to that provided by the print material and prerecorded audio material. To activate the recording function of the recordable audio device, the record button is depressed and held down. The recording can then be replayed by depressing the play/stop button once, and replay can be stopped by depressing the play stop button a second time. The user wishes to make a new recording, the record button may be depressed again. If the user wishes to add voice-recorded material to that already recorded on the recordable audio device, the add recording button is depressed and held down. The add recording function will add voice-recorded material to that already contained on the recordable audio device until the capacity of the audio device is exhausted. All recordings may then be replayed by use of the play/stop button.

Example 2

Figure 4A:
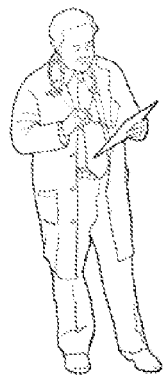
FIGS. 4A-C shows an embodiment of the methods of the invention, wherein a healthcare provider dictates specific instructions or health information or instructions onto the recordable microprocessor of the system of the invention (4A); wherein the system is given to the recipient, usually the patient, caregiver or another healthcare provider (4B); and wherein the recipient listens to prerecorded and unique information to clarify print instructions, encourage self-management of their disease, and receive messages from the healthcare provider.
Figure 4B:
Figure 4C:
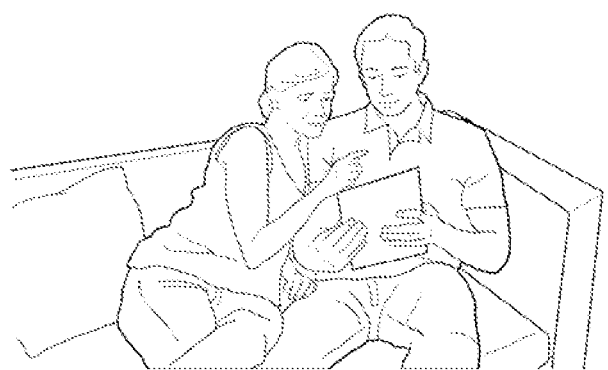

The invention as illustrated, comprising the housing with print material, an embedded prerecorded audio device, and embedded recordable audio device, would likely be accomplished by a manufacturer. The voice-recorded material on the prerecorded audio device is furnished by the manufacturer. The invention is purchased at this point by a physician, insurer, hospital system or other healthcare provider. A healthcare provider may then further add content to the system, including dictating patient-specific instructions or health information on to the recordable microprocessor (FIG. 4A). Thereafter, the system is given to the recipient, usually the patient, caregiver or another healthcare provider (FIG. 4B), wherein the recipient listens to prerecorded and unique information to clarify print instructions, encourage self-management of their disease, and receive messages from the healthcare provider (FIG. 4C). The recipient may also add additional voice-recorded material to that provided by the first healthcare provider.

Example 3

The various embodiments of the invention, including methods of the invention further include the capability of allowing a patient to use a "teach back" process or function of the invention. As one skilled in the art will ascertain, the "teach back" process is a method frequently used by clinicians (e.g. such as upon discharge from a clinicians' care) where the clinician says what the patient needs to do, then asks the patient to repeat back what they need to do. In particular, according to the invention, a patient may be asked to record the instructions they have been provided to effectively demonstrate to a healthcare provider, through a "teach back" process, that the patient has acquired the requisite knowledge and/or health information. The teach back process may be repetitively used with a patient during health coaching sessions.

In addition to demonstrating the patient's knowledge and/or health information obtained through teach back methods, this type of method of use is also demonstrated to beneficially allow a patient to establish and record various healthcare goals and/or commitments applicable to their treatment and/or care plan. Such goals and/or commitments are then readily available to a patient for repetition and reminder in order to achieve better outcomes.

The inventions being thus described, it will be obvious that the same may be varied in many ways. Such variations are not to be regarded as a departure from the spirit and scope of the inventions and all such modifications are intended to be included within the scope of the following claims. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below so that the invention may be more readily understood.

It should be noted that, as used in this specification and the appended claims, the singular forms "a," "an," and "the" include plural referents unless the content clearly dictates otherwise. Thus, for example, reference to a system containing "a component" includes a system having two or more components. It should also be noted that the term "or" is generally employed in its sense including "and/or" unless the content clearly dictates otherwise.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

What is claimed:

1. A system for combining audio technology with print material to deliver information about health, wellness, prescriptions and/or a disease state or condition, comprising:
   at least one audio device that provides audio content, wherein said audio content includes prerecorded and recordable audio information, wherein said audio device stores, records and delivers audio information to a patient or caregiver, and wherein said prerecorded audio information is provided by a third party;
   print material, wherein said print material provides health information and instructions to a patient or caregiver, wherein said print material further provides one or more of photographs, drawings, barcodes, and graphic material for marketing of a healthcare provider, and wherein said print material further includes space for a patient or caregiver to chart content and make notes;
   a housing system combining said print material and said audio device,
      wherein the audio device or print material is removable from the housing system without losing the ability to deliver information,
      wherein print material and audio content is accessible by said patient or caregiver for receiving health information about said patient,
   wherein said audio device is configured to deliver audio information about health, wellness, prescriptions and/or a disease state or condition of said patient, and
   wherein said audio device comprises at least one playback microprocessor and at least one recording microprocessor, a microphone, a power source, a plurality of record buttons, and a housing, wherein said microprocessors are comprised of an integrated circuit chip, and
   a play/stop button connected to the system housing, wherein the selective activation of the play/stop button enables the playback microprocessor to play said audio content; and
   a first record button connected to the system housing, wherein the selective activation of the first record button enables the recording microprocessor to record first audio information via said microphone,
   a second record button connected to the system housing, wherein the selective activation of the second record button enables the recording microprocessor to record second audio information via said microphone, wherein said recording of said second audio information adds the second audio information to the first audio information,
a third record button connected to the system housing, wherein the selective activation of the third record button enables the recording microprocessor to record third audio information via said microphone, wherein said recording of said third audio information overwrites the first audio information.

2. The system of claim 1, wherein said integrated circuit chip microprocessor is a complementary metal oxide semiconductor.

3. The system of claim 1, wherein said print material comprises print material selected from the group consisting of paper sheet, booklet, pamphlet, cardstock, plastic and combinations thereof.

4. The system of claim 1, wherein said microprocessors are housed in a slot or plurality of slots in said system housing.

5. The system of claim 1, wherein a plurality of audio devices are combined in said system to provide a patient-specific system for delivering health information.

6. The system of claim 1, wherein the third party is a manufacturer that provides said prerecorded audio information.

7. The system of claim 1, wherein said prerecorded audio source and/or recordable audio source is capable of being easily removed, inserted, and retained within said housing system.

8. The system of claim 1, wherein the power source is comprised of batteries, solar batteries kinetic energy harvesters or external power adapters.

9. The system of claim 1, wherein the recording is terminated by at least one of releasing the record button or a second selective activation of the record button.

10. The system of claim 1, wherein, via the audio device, the patient records audio information comprising audio information instructions provided by the device.

11. A method for storing, recording and delivering audio technology with print material to deliver health information to a patient or caregiver in need thereof, comprising:
providing at least one audio device that provides audio content to said patient or caregiver, wherein said audio content includes prerecorded and recordable audio information, wherein said audio device stores, records and delivers audio information to said patient or caregiver, and wherein said prerecorded audio information is provided by a third party;
providing print material to said patient or caregiver, wherein said print material provides health information and instructions to a patient or caregiver, wherein said print material further provides one or more of photographs, drawings, barcodes, and graphic material for marketing of a healthcare provider, and wherein said print material further includes space for a patient or caregiver to chart content and make notes;
wherein said audio device and print material is housed within a housing system configured to deliver information about health, wellness, prescriptions and/or a disease state or condition of said patient,
wherein the audio device or print material is removable from the housing system without losing the ability to deliver information,
wherein said audio device comprises at least one playback microprocessor and at least one recording microprocessor, a microphone, a power source, a plurality of record buttons, and a housing,
wherein said microprocessors are comprised of an integrated circuit chip, and
accessing said print material and audio content by said patient or caregiver to receive health information about said patient, wherein accessing said audio content comprises selectively activating the playback microprocessor via use of a play/stop button; and
recording first audio information by a patient or caregiver by selectively activating the recording microprocessor via use of a first record button, and entering audio information via said microphone;
recording second audio information by a patient or caregiver by selectively activating the recording microprocessor via use of at least one of a second record button or a third record button,
wherein use of the second record button records second audio information without erasing the first audio information; and
wherein use of the third record button overwrites the first audio information with the second audio information.

12. The method of claim 11, wherein said prerecorded audio source and/or recordable audio source is capable of being easily removed, inserted, and retained within said housing system.

13. The method of claim 11, wherein said print material comprises print material selected from the group consisting of paper sheet, booklet, pamphlet, cardstock, plastic and combinations thereof.

14. The method of claim 11, wherein a plurality of audio devices are combined in said system to provide a patient-specific system for delivering health information.

15. The method of claim 11, wherein said integrated circuit chip microprocessor is a complementary metal oxide semiconductor.

16. The method of claim 11, wherein said microprocessors are housed in a slot or plurality of slots in said system housing.

17. The method of claim 11, wherein the third party is a manufacturer that provides said prerecorded audio information.

18. The method of claim 11, wherein the power source is comprised of batteries, solar batteries kinetic energy harvesters or external power adapters.

19. The method of claim 11, wherein the recording is terminated by at least one of releasing the record button or a second use of the record button.

20. The method of claim 11, wherein, via the audio device, the patient records audio information comprising audio information instructions provided by the device.

* * * * *